US00PP11306P

United States Patent [19]

Brown et al.

[11] Patent Number: Plant 11,306

[45] Date of Patent: Mar. 21, 2000

[54] AGLAONEMA PLANT NAMED 'CASSANDRA'

[75] Inventors: B. Frank Brown; Cleofar P. Millare, both of Valkaria, Fla.

[73] Assignee: Sunshine Foliage World, Zolfo Springs, Fla.

[21] Appl. No.: 09/114,123

[22] Filed: Jul. 13, 1998

[51] Int. Cl.[7] ..... A01H 5/00

[52] U.S. Cl. ..... Plt./376

[58] Field of Search ..... Plt./376

*Primary Examiner*—Howard J. Locker
*Assistant Examiner*—Kent L. Bell
*Attorney, Agent, or Firm*—C. A. Whealy

[57] ABSTRACT

A new and distinct cultivar of Aglaonema named 'Cassandra' particularly characterized by its upright and outwardly arching plant habit; uniform plant habit; good production of divisions; short internodes with numerous leaves giving plants a very full and dense appearance; upper leaf surfaces that are glossy silver green with dark green random spots and whitish-green to white midrib; large, oblong, flat leaves with white petioles which contrast well with the leaves; tolerance to low temperatures; and resistance to diseases common to Aglaonema.

1 Drawing Sheet

BACKGROUND OF THE INVENTION

The present invention relates to a new and distinct cultivar of Aglaonema plant, botanically known as Aglaonema hybrid, and hereinafter referred to by the cultivar name 'Cassandra'.

The new Aglaonema is a product of a planned breeding program conducted by the Inventors in Valkaria, Fla. The objective of the breeding program was to develop new Aglaonemas with unique and interesting leaf patterns and white petioles that readily produced divisions.

The new Aglaonema originated from a cross made by the Inventors of the *Aglaonema nitidum curtisii* cv. 'Mona Lisa' (not patented) as the male, or pollen, parent with the Aglaonema hybrid cv. 'Manila Pride' (not patented) as the female, or seed, parent. The cultivar 'Cassandra' was discovered and selected by the Inventors in April, 1989 as a seedling within the progeny of the stated cross in a controlled environment in Valkaria, Fla.

Plants of the new Aglaonema differ from plants of the male parent, the cultivar 'Mona Lisa', in leaf pattern and petiole color. Plants of the new Aglaonema differ from plants of the female parent, the cultivar 'Manila Pride', in petiole color and growth rate.

Asexual propagation of the new cultivar by divisions at Valkaria, Fla. has shown that the unique features of this new Aglaonema plant are stable and reproduced true to type in successive generations.

SUMMARY OF THE INVENTION

The new Aglaonema has not been observed under all possible environmental conditions. The phenotype may vary somewhat with variations in environment such as temperature, light intensity, fertilizer rate, and/or irrigation amount and frequency without, however, any variance in genotype.

The following traits have been repeatedly observed and are determined to be the unique characteristics of 'Cassandra'. These characteristics in combination distinguish 'Cassandra' as a new and distinct cultivar:

1. Plants of the new Aglaonema are upright and outwardly arching in plant habit.

2. Plants of the new Aglaonema maintain uniform plant habit and typically grow to about 70 cm in height.

3. Plants of the new Aglaonema readily produce divisions.

4. Plants of the new Aglaonema have short internodes with numerous leaves giving plants a very full and dense appearance.

5. The upper surfaces of mature leaves of plants of the new Aglaonema are glossy silver green with dark green random spots and whitish-green to white midrib.

6. Leaves of the new Aglaonema are large, oblong and flat and have white petioles which contrast well with the leaves.

7. Plants of the new Aglaonema are very tolerant of low temperatures, that is, ambient temperatures of about 4° C. do not cause foliar damage.

8. Plants of the new Aglaonema are resistant to diseases common to Aglaonema.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical plant of 'Cassandra' in a 25.5-cm container.

The photograph at the bottom of the sheet comprises a close-up view of the upper and lower surfaces of mature leaves. Leaf colors in the photographs may appear different from the actual colors due to light reflectance.

DETAILED BOTANICAL DESCRIPTION

The following observations, measurements and comparisons describe plants grown in Zolfo Springs, Fla., under a polypropylene-covered shadehouse and conditions which closely approximate those used in horticultural practice. Plants were grown under day temperatures ranging from 21 to 38° C. and night temperatures ranging from 7 to 21° C. The polypropylene shade provided a 84 percent decrease in ambient light level. In the following description, color references are made to The Royal Horticultural Society Colour Chart except where general terms of ordinary dictionary significance are used.

Botanical Classification: Aglaonema hybrid cultivar 'Cassandra'.

Parentage:

*Male, or pollen, parent.*—*Aglaonema nitidum curtisii* cultivar 'Mona Lisa'.

*Female, or seed, parent.*—Aglaonema hybrid cultivar 'Manila Pride'.

Propagation:

*Type.*—By division and by cuttings.

*Time to initiate roots.*—About 21 and 40 days at 30 and 20° C., respectively.

*Time to develop roots.*—About 30 and 60 days at 30 and 20° C., respectively.

*Rooting habit.*—Large fleshy and fibrous roots.

Plant description:

*Plant shape.*—Upright and outwardly arching.

*Growth habit.*—Erect when young, becoming outwardly arching. Appropriate for 25.5-cm and larger containers. Plants readily produce divisions.

*Plant size.*—Height, soil surface to top of leaf canopy: About 62 cm. Width: About 88 cm.

*Plant vigor.*—Moderate, rapid growth rate.

*Stem description.*—Diameter at soil surface: About 2.5 cm. Internode length: About 1 cm. Color, mature: Mostly white with occasional green areas.

*Foliage description.*—Shape: Oblong. Length, fully expanded: About 27 cm. Width, fully expanded: About 10 cm. Margin: Entire. Apex: Acuminate. Base: Cuneate. Aspect: Flat. Texture: Leathery, smooth, glabrous, glossy on both surfaces. Color: Young, upper surface: Background: 194A/194B. Dark green spots/streaks: 147A. Green spots/streaks: 146B, 147B, and 144A. Yellowish green to light green to white spots: Near to midvein and follow lateral veins, 154A to 154D, 145D, and 155D. Midvein: Speckled light green to yellow green to white. Young, lower surface: Background: Close to 144A. White and light green spots/streaks: 145D to 155D. Midvein: 145D to 155D. Mature, upper surface: Background: 194A/close to 198A, 191A, and 189A. Dark green spots: 147A or darker than 147A. Green spots: 146A and occasionally 144A. Yellowish green to light green to white spots: Near to midvein and follow lateral veins, 154A to 154D, 145D, and 155D. Midvein: Speckled green and white. Mature, lower surface: Background: Close to 146A. White and light green spots/streaks: 145D/155D. Midvein: Whitish green, 145D, to white, 155D. Petiole length, primary shoot: About 20.5 cm. Petiole diameter at apex: About 5 mm. Petiole diameter at base: About 1.75 cm. Petiole wing: Apparent on lower 60 percent of mature leaf petiole, about 12 cm in length and about 6 mm in width. Petiole color: Whitish green, 145D, to white, 155D, with rare green streaks and spots.

*Inflorescence.* Typical of Aglaonema, no commercial significance.

Disease Tolerance: Plants of the new Aglaonema are resistant to diseases common to Aglaonema.

Low temperature tolerance: Plants of the new Aglaonema are very tolerant of low temperatures, that is, ambient temperatures of about 4° C. do not cause foliar damage.

It is claimed:

1. A new and distinct cultivar of Aglaonema plant named 'Cassandra', as illustrated and described.

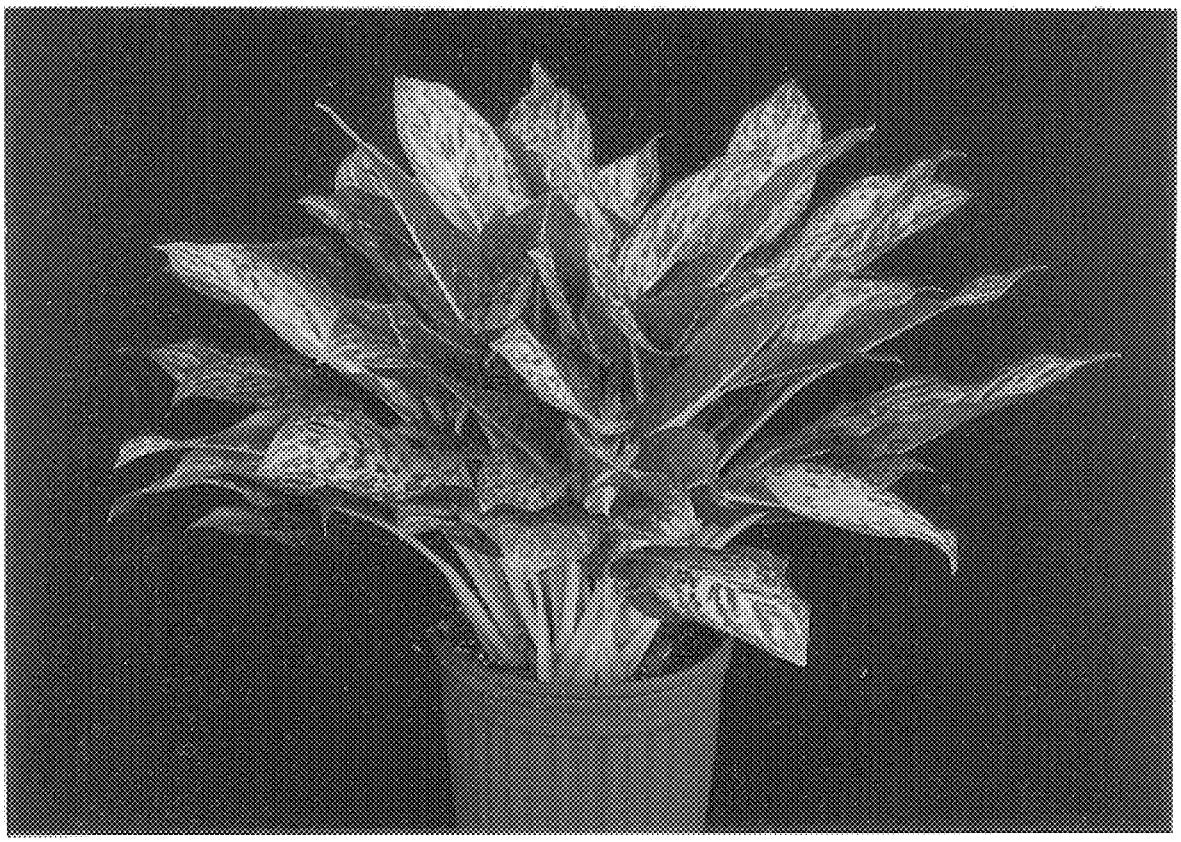
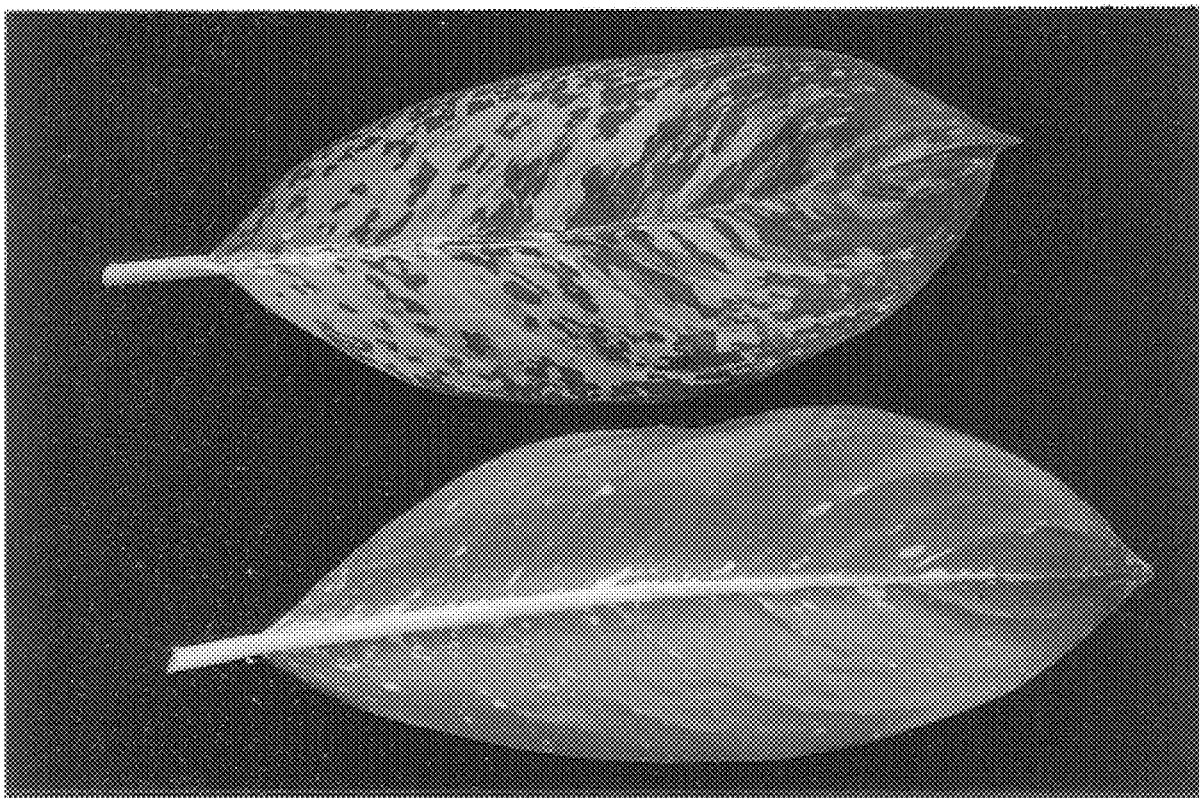

* * * * *